(12) United States Patent
Miyai et al.

(10) Patent No.: US 9,468,877 B2
(45) Date of Patent: Oct. 18, 2016

(54) EXHAUST GAS ANALYZING APPARATUS

(71) Applicant: HORIBA, Ltd., Kyoto (JP)

(72) Inventors: Masaru Miyai, Kyoto (JP); Tomoshi Yoshimura, Kyoto (JP); Manabu Ito, Kyoto (JP)

(73) Assignee: Horiba, Ltd., Kyoto (JP)

( * ) Notice: Subject to any disclaimer, the term of this patent is extended or adjusted under 35 U.S.C. 154(b) by 54 days.

(21) Appl. No.: 13/899,952

(22) Filed: May 22, 2013

(65) Prior Publication Data

US 2013/0312615 A1    Nov. 28, 2013

(30) Foreign Application Priority Data

May 22, 2012    (JP) .................. 2012-117042

(51) Int. Cl.
| | |
|---|---|
| *B01D 53/22* | (2006.01) |
| *B01D 59/12* | (2006.01) |
| *B01D 46/00* | (2006.01) |
| *G01N 1/22* | (2006.01) |

(52) U.S. Cl.
CPC ......... *B01D 46/0058* (2013.01); *G01N 1/2247* (2013.01); *G01N 1/2252* (2013.01)

(58) Field of Classification Search
CPC ............... F01N 13/011; F01N 13/107; B01D 2255/9045; B01D 46/0068
See application file for complete search history.

(56) References Cited

U.S. PATENT DOCUMENTS

| | | | |
|---|---|---|---|
| 2006/0070359 A1* | 4/2006 | Sellers et al. ................... | 55/303 |
| 2007/0294999 A1* | 12/2007 | Yoshizaki et al. ............. | 60/274 |
| 2008/0022752 A1 | 1/2008 | Hodzic et al. | |
| 2008/0127506 A1 | 6/2008 | Han et al. | |
| 2008/0184679 A1* | 8/2008 | Jirele et al. ..................... | 55/283 |
| 2009/0064664 A1 | 3/2009 | Hirata et al. | |
| 2009/0113856 A1* | 5/2009 | Cooper et al. .................. | 55/283 |
| 2009/0114095 A1 | 5/2009 | Hanson et al. | |
| 2009/0120070 A1 | 5/2009 | Hirata et al. | |

(Continued)

FOREIGN PATENT DOCUMENTS

| | | |
|---|---|---|
| CN | 1309232 A | 8/2001 |
| CN | 1890547 A | 1/2007 |

(Continued)

OTHER PUBLICATIONS

Office Action dated Jan. 6, 2015 issued for Japanese patent application No. 2012-117042, 3 pgs.

(Continued)

*Primary Examiner* — Amber R Orlando
(74) *Attorney, Agent, or Firm* — Brooks Kushman P.C.

(57) ABSTRACT

An exhaust gas analyzing apparatus provided a first filter flow path with a first filter, a second filter flow path provided with a second filter, an exhaust gas analyzing part for analyzing exhaust gas passing through the first filter or the second filter, a flow path switching mechanism for switching between the first filter flow path and the second filter flow path. A pulse purge mechanism is provided for supplying purge gas to the filters, in the filter flow paths, in a pulsed manner, and in the case where a pressure difference between an upstream side and a downstream side of the filter provided in one filter flow path where the exhaust gas flows becomes equal to or larger than a predetermined value, the one filter flow path is switched to the other one, and purge gas is supplied to the filter provided in the one filter flow path in the pulsed manner.

4 Claims, 4 Drawing Sheets

(56) References Cited

U.S. PATENT DOCUMENTS

2010/0242443 A1    9/2010  Kodama et al.
2013/0276628 A1*  10/2013  Chalabi et al. .................... 95/9

FOREIGN PATENT DOCUMENTS

| | | |
|---|---|---|
| CN | 101171407 A | 4/2008 |
| CN | 101220982 A | 7/2008 |
| CN | 101292077 A | 10/2008 |
| CN | 101439251 A | 5/2009 |
| CN | 101788486 A | 7/2010 |
| CN | 101896699 A | 11/2010 |
| CN | 202614743 U | 12/2012 |
| GB | WO2011124885 * | 10/2011 |
| JP | 62-126748 U | 11/1987 |
| JP | 64-079641 A | 3/1989 |
| JP | 01-144427 U | 10/1989 |
| JP | 06-146858 A | 5/1994 |
| JP | 2000-088718 | 3/2000 |
| JP | 2002-250771 | 9/2002 |
| JP | 2003-344244 | 12/2003 |
| JP | 2004-138475 | 5/2004 |
| JP | 2006153746 | 6/2006 |
| JP | 2006-250738 | 9/2006 |
| JP | 2007-248114 | 9/2007 |
| JP | 2009-510448 A | 3/2009 |
| JP | 2009-138704 A | 6/2009 |
| JP | 2009-222660 | 10/2009 |
| JP | 4513861 B2 | 7/2010 |
| WO | 2007-041274 A2 | 4/2007 |

OTHER PUBLICATIONS

Office Action dated Sep. 1, 2015 issued for Chinese patent application No. 201310176762.2, 12 pgs.

* cited by examiner

EXHAUST GAS ANALYZING APPARATUS

CROSS-REFERENCE TO RELATED APPLICATION

This application claims priority to JP Application No. 2012-117042, filed on May 22, 2012, the disclosure of which is incorporated in its entirety by reference herein.

TECHNICAL FIELD

The present invention relates to an exhaust gas analyzing apparatus for analyzing exhaust gas discharged from internal combustion engines of vehicles and the like or external combustion engines of steam turbines and the like.

BACKGROUND ART

As described in Japanese Patent JPA 2006-153746, in a conventional exhaust gas analyzing apparatus, an introduction path for introducing exhaust gas discharged from an engine installed in a test chamber is equipped with a dust filter for removing dusts and soot in the exhaust gas. The dust filter is clogged with adhered dusts and soot and thus, needs to be replaced periodically (for example, every eight hours).

However, since the dust filter is often arranged in the test chamber, a user need to enter the test chamber to replace the dust filter. The test chamber is under high temperatures due to activation of the engine of the vehicle or the like, and moreover, the dust filter is arranged in the vicinity of the engine or the exhaust pipe under high temperatures. Accordingly, the user has to replace the dust filter in a high-temperature environment and bear an enormous load. Moreover, the operation of replacing the dust filter is performed in the vicinity of the engine or the exhaust pipe under high temperatures, which is dangerous. The operation of replacing the dust filter can be performed after the engine or the exhaust pipe is cooled. In this case, however, it takes a long time to start next measurement of the exhaust gas.

In recent years, continuous measurement (for example, 24-hour continuous measurement and 48-hour continuous measurement) of the engine of the vehicles and the like has been demanded. However, as described above, continuous measurement needs to be stopped to replace the dust filter. Therefore, it is difficult to make desired continuous measurement.

SUMMARY OF INVENTION

Technical Problem

The present invention is conceived to solve all of the above-mentioned problems, and its object is to substantially eliminate an operation of replacing a filter by a user moving to a place where the filter is installed, such as a test chamber in which an engine is placed, thereby enabling continuous measurement of exhaust gas discharged from the engine.

Solution to Problem

An exhaust gas analyzing apparatus for analyzing exhaust gas according to the present invention includes a first filter flow path provided with a first filter for passing the exhaust gas therethrough and a first sensor for detecting clogging of the first filter; a second filter flow path provided with a second filter for passing the exhaust gas therethrough and a second sensor for detecting clogging of the second filter; an exhaust gas analyzing part for analyzing the exhaust gas passing through the first filter or the second filter; a flow path switching mechanism for selectively passing the exhaust gas to the first filter flow path or the second filter flow path; and a pulse purge mechanism provided in each of the filter flow paths, the mechanism supplying purge gas to each of the filters in a pulsed manner, and in the case where an output value of the sensor provided in one filter flow path, to which the flow path switching mechanism passes the exhaust gas, falls outside a predetermined range, the one filter flow path, to which the flow path switching mechanism passes the exhaust gas, is switched to the other filter flow path, and the pulse purge mechanism supplies the purge gas to the filter provided in the one filter flow path in a pulsed manner.

With such configuration, in the case where the output value of the sensor falls outside the predetermined range due to clogging of the filter provided in one filter flow path in which the exhaust gas flows, the filter flow path in which the exhaust gas flows is switched to the other filter flow path, enabling continuous measurement of the exhaust gas. Further, following switching to the other filter, the purge gas is supplied in the pulsed manner to one filter that has clogging and requires washing and therefore, the one filter can be washed and recycled without being replaced. By sequentially switching between the first filter and the second filter in this manner, the need to suspend measurement for filter replacement is eliminated, enabling continuous measurement. Furthermore, since the pulse purge mechanism supplies the purge gas in the pulsed manner, the high-pressure gas can be efficiently supplied to the filter without increasing a capacity of a compressor of the pulse purge mechanism.

Examples of the sensor (the first sensor, the second sensor) provided in the filter flow path (the first filter flow path, the second filter flow path) include (1) a pressure sensor for detecting a pressure difference between the upstream side and the downstream side of the filter, (2) a pressure sensor for detecting the pressure of either an upstream side or a downstream side of the filter, (3) a flow rate sensor for detecting the flow rate in the filter, and (4) a combination of the pressure sensor for detecting the pressure of either the upstream side or the downstream side of the filter and the flow rate sensor for detecting the flow rate in the filter. At this time, the output value of the sensor falling outside the predetermined range means that the pressure difference acquired by the pressure sensor becomes equal to or larger than a predetermined value in the case of (1), the pressure on the upstream side of the filter, which is acquired by the pressure sensor, becomes equal to or larger than a predetermined value or the pressure on the downstream side of the filter, which is acquired by the pressure sensor, becomes equal to or smaller than the predetermined value in the case of (2), the flow rate acquired by the flow rate sensor becomes equal to or smaller than a predetermined value in the case of (3), and the flow rate acquired by the flow rate sensor becomes equal to or smaller than a predetermined value with respect to the pressure acquired by the pressure sensor in the case of (4).

In the case where the flow path switching mechanism switches the flow path between the first filter flow path and the second filter flow path, since the purge gas remains in the filter as a destination, the exhaust gas is diluted with the purge gas, and the concentration of components in the exhaust gas measured by the exhaust gas analyzing part temporarily lowers. For this reason, when the flow path is automatically switched while focusing on variation in the component concentration with time, the usability deteriorates instead. To solve this problem, it is preferred that the flow path switching mechanism can select the switching timing from an automatic mode of automatically performing switching in the case where the output value of the sensor falls outside the predetermined range and a manual mode of manually performing switching by the user. Since the automatic mode or the manual mode can be selected, by selecting the manual mode when focusing on variation in the component concentration with time, it is possible to prevent the flow path from being automatically switched to temporarily lower the component concentration.

In the case where the one filter flow path is switched to the other filter flow path, when the other filter as the switching destination is under low temperatures, the measured components in the exhaust gas are aggregated, exerting a negative effect on a measurement result. Thus, it is desired that, before the flow path switching mechanism switches the filter flow path in which the exhaust gas flows to the other filter flow path, the filter provided in the other filter flow path is heated in advance.

It is desired that, in the case where the pulse purge mechanism supplies the purge gas in the pulsed manner, the purge gas supplied in the pulsed manner heats the filter. By supplying the purge gas to the heated filter, a filtrated material adhered to the filter can be easily removed.

Advantageous Effects of Invention

According to the present invention thus configured, for example, the operation of moving to a filter installation site such as a test chamber in which the engine is installed and replacing the filter is substantially eliminated, enabling continuous measurement of the exhaust gas discharged from the engine.

DESCRIPTION OF EMBODIMENTS

An embodiment of an exhaust gas analyzing apparatus according to the present invention will be described below referring to figures.

An exhaust gas analyzing apparatus 1 in the present embodiment is provided in a test chamber in which an engine of a vehicle not shown to analyze exhaust gas discharged from the engine. The exhaust gas analyzing apparatus 1 exchanges various data including analysis data and schedule data with a central manager in a measurement chamber separated from the test chamber via, for example, LAN.

Figure 1:
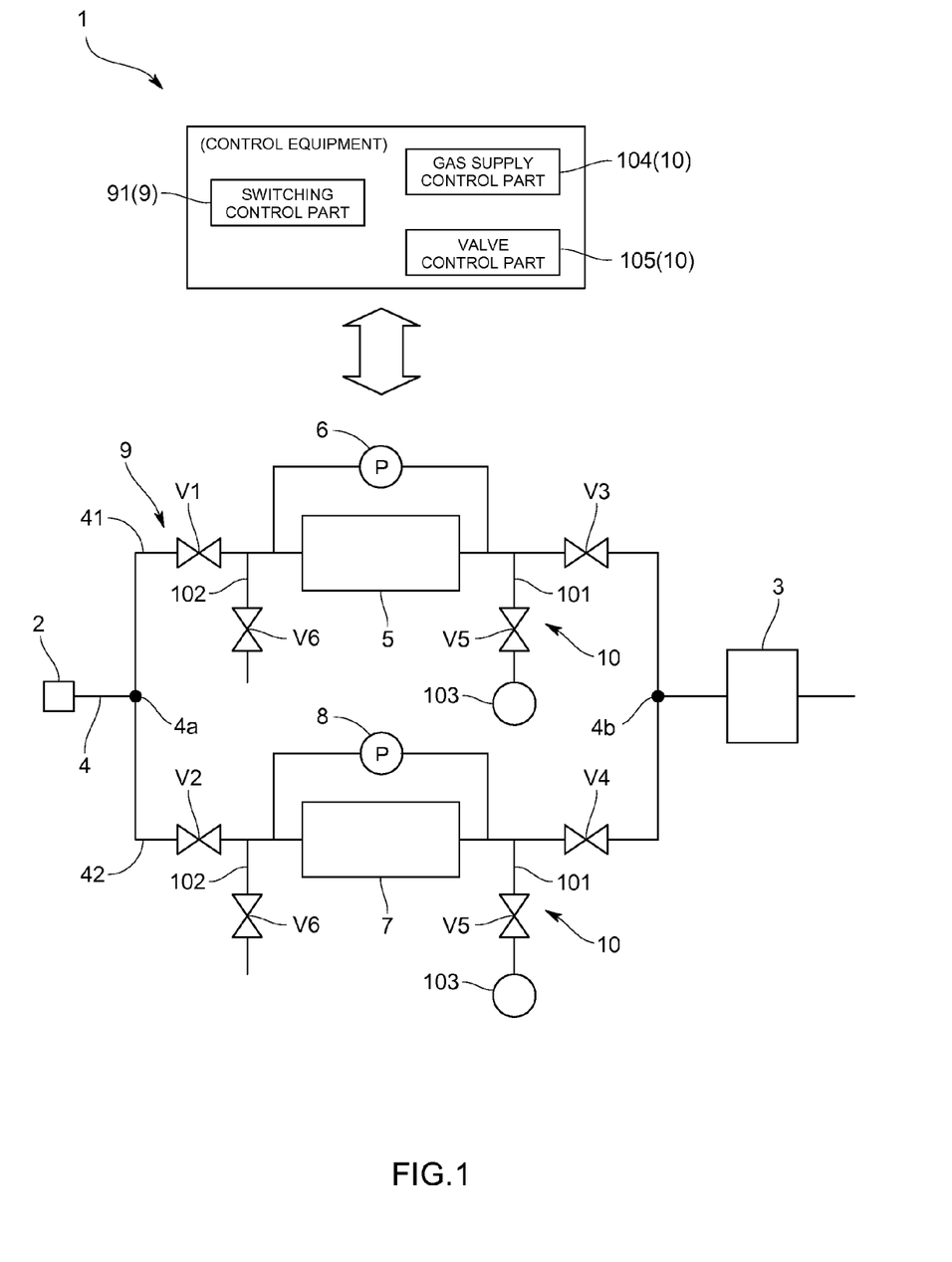
FIG. 1 is a diagram schematically showing a configuration of an exhaust gas analyzing apparatus in the present embodiment.

Specifically, as shown in FIG. 1, the exhaust gas analyzing apparatus 1 includes an introduction port 2 for introducing exhaust gas discharged from the engine, an exhaust gas analyzing part 3 for analyzing the exhaust gas introduced from the introduction port 2, and an introduction path 4 for connecting the introduction port 2 to the exhaust gas analyzing part 3 and guiding the exhaust gas introduced from the introduction port 2 to the exhaust gas analyzing part 3. The exhaust gas analyzing part includes a plurality of different gas analyzers having different measurement principles, thereby individually measuring components contained in the exhaust gas, such as HC, NOx, CO, and CO2.

The introduction path 4 includes a first filter flow path 41 provided with a first filter 5 for passing exhaust gas therethrough and a first pressure sensor 6 for detecting a pressure difference between an upstream side and a downstream side of the first filter 5, and a second filter flow path 42 provided with a second filter 7 for passing the exhaust gas therethrough and a second pressure sensor 8 for detecting a pressure difference between an upstream side and a downstream side of the second filter 7. The first filter 5 and the second filter 7 each are, for example, a filter made of a fibrous material formed of glass wool, or a surface filtration filter produced by winding a sheet body, into which a linear body made of metal such as stainless steel is knitted, in a cylindrical fashion. The surface filtration filter can be easily washed, in the case where pulse purge mechanisms 10 described later supplies purge gas from the downstream side in a pulsed manner.

The first filter flow path 41 and the second filter flow path 42 are provided between a branch point 4a of the introduction path 4 on the upstream side and a meeting point 4b of the introduction path 4 on the downstream side in parallel with each other. On a way to the exhaust gas analyzing part 3 in the introduction path 4, a hot hose for keeping the temperature of the exhaust gas at about 130° C. and a flow rate control part (for example, regulator) are attached.

The introduction path 4 is further provided with a flow path switching mechanism 9 for selectively passing the exhaust gas to the first filter flow path 41 or the second filter flow path 42, and the pulse purge mechanisms 10 that are provided in the respective filter flow paths 41, 42 and supply the purge gas to the filters 5, 6 from the downstream side in the pulsed manner. The pulse purge mechanisms 10 constitute filter washing mechanisms for washing the filters 5, 6.

The flow path switching mechanism 9 has, as shown in FIG. 1, a first upstream side on-off valve V1 provided on the upstream side of the first filter 5 in the first filter flow path 41, a second upstream side on-off valve V2 provided on the upstream side of the second filter 7 in the second filter flow path 42, and a switching control part 91 for controlling the first and second upstream side on-off valves V1, V2. The first upstream side on-off valve V1 and the second upstream side on-off valve V2 each are, for example, an electromagnetic valve. The switching control part 91 controls open/close of the first upstream side on-off valve V1 and the second upstream side on-off valve V2 to "first upstream side on-off valve V1: open, second upstream side on-off valve V2: close" or "first upstream side on-off valve V1: close, second upstream side on-off valve V2: open", thereby selectively passing the exhaust gas to either the first filter flow path 41 or the second filter flow path 42. Specifically, the switching control part 91 acquires pressure data from the pressure sensors 6, 8 of the filter flow paths 41, 42 through which the exhaust gas flows, compares a measurement value (pressure difference) indicated by the pressure data with a pre-input predetermined threshold, and in the case where the measurement value is larger than the predetermined threshold, controls the upstream side on-off valves V1, V2 to switch between the filter flow paths 41, 42 through which the exhaust gas flows. The predetermined threshold is a reference pressure difference for switching between the filter flow paths 41, 42 and specifically, is a pressure difference indicating that the filters 5, 7 are clogged.

In the present embodiment, since the pulse purge mechanisms 10 are provided as described later, first and second downstream side on-off valves V3, V4 are also provided on the downstream side of the first filter 5 and the downstream side of the second filter 7, respectively. The first and second downstream side on-off valves V3, V4 each are for example, an electromagnetic valve. The switching control part 91 sets the operation of the first downstream side on-off valve V3 to be the same as the operation of the first upstream side on-off valve V1, and the operation of the second downstream side on-off valve V4 to be the same as the operation of the second upstream side on-off valve V2. That is, the first filter flow path 41 is tightly shut by closing the first upstream side on-off valve V1 and the first downstream side on-off valve V3. Similarly, the second filter flow path 42 is tightly shut by closing the second upstream side on-off valve V2 and the second downstream side on-off valve V4.

As shown in FIG. 1, the pulse purge mechanism 10 provided in each of the filter flow paths 41, 42 includes a purge gas introduction path 101 connected to the downstream side of the filters 5, 7 in the filter flow paths 41, 42, a purge gas lead-out path 102 connected to the upstream side of the filters 5, 7, a purge gas supplying part 103 for supplying the purge gas to the purge gas introduction path 101, and a gas supply control part 104 for controlling the operation of the purge gas supplying part 103 to supply the purge gas in the pulsed manner. The purge gas introduction path 101 is connected to the upstream side of each of the first and second downstream side on-off valves V3, V4 and is provided with an on-off valve V5. The purge gas lead-out path 102 is connected to the downstream side of the first and second upstream side of each of on-off valves V1, V2, and is provided with an on-off valve V6. The on-off valves V5, V6 each are, for example, an electromagnetic valve, and is controlled in opening/closing by a valve control part 105. The purge gas supplying part 103 has a compressor for compressing the purge gas into high-pressure gas.

In the case where the filters 5, 7 are washed, the valve control part 105 opens the on-off valves V5, V6 provided in the purge gas introduction paths 101 and the purge gas lead-out paths 102, and the gas supply control part 104 controls the purge gas supplying parts 103, thereby supplying the high-pressure purge gas from the downstream side of the filters 5, 7, that is, in a direction reverse to the exhaust gas flowing direction one or more times in the pulsed manner. Supplying in the pulsed manner means that the purge gas is supplied for a few seconds (for example, one second). The number of times of such pulsed supply varies depending on a type of the engine (type of the exhaust gas). At this time, both of the upstream side on-off valve (V1 or V2) and the downstream side on-off valve (V3 or V4) in the filter flow path (41 or 42) supplying the purge gas are closed to prevent the purge gas from flowing into the filter flow path, through which the exhaust gas is flowing, and diluting the exhaust gas. That is, for example, when the purge gas is supplied to the first filter 5 in the first filter flow path 41, the purge gas is not flown to the second filter flow path 42.

Control equipment including the switching control part 91 of the flow path switching mechanism 9, and the gas supply control part 104 and the valve control part 105 of the pulse purge mechanisms 10 may be configured to function as one computer (including, for example, a CPU, a memory, an input/output interface, an AD converter, and a display), or function as a plurality of physically-separated computers.

Next, the operation of the exhaust gas analyzing apparatus 1 thus configured will be described.

Figure 2:
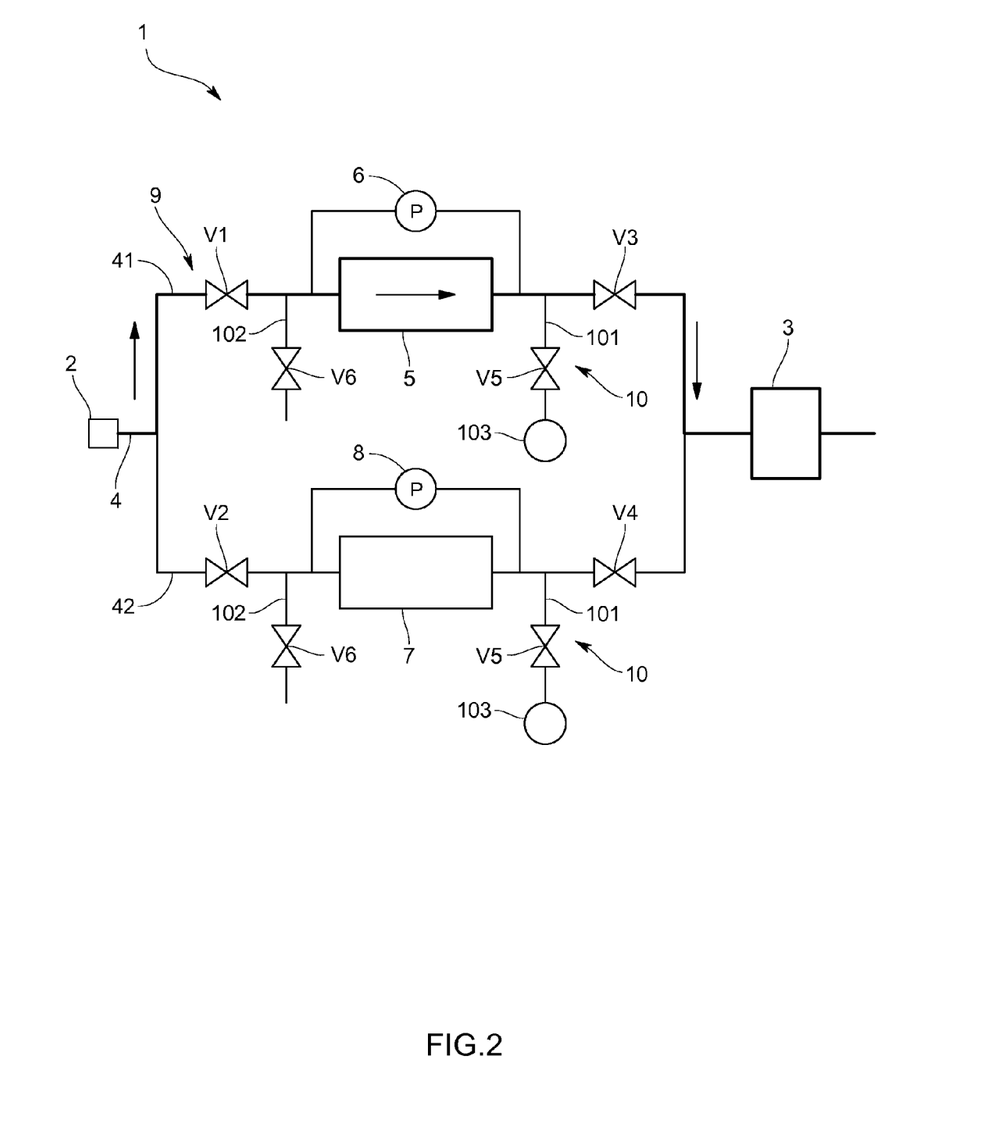
FIG. 2 is a diagram showing a state where the exhaust gas flows in a first filter flow path.

As shown in FIG. 2, in the case where the exhaust gas is passed to the first filter flow path 41 and the exhaust gas flowing in the first filter flow path 41 is analyzed by the exhaust gas analyzing part 3, the first pressure sensor 6 detects the pressure difference between the upstream side and the downstream side of the first filter 5, and the pressure data is inputted into the switching control part 91 of the flow path switching mechanism 9.

Figure 3:
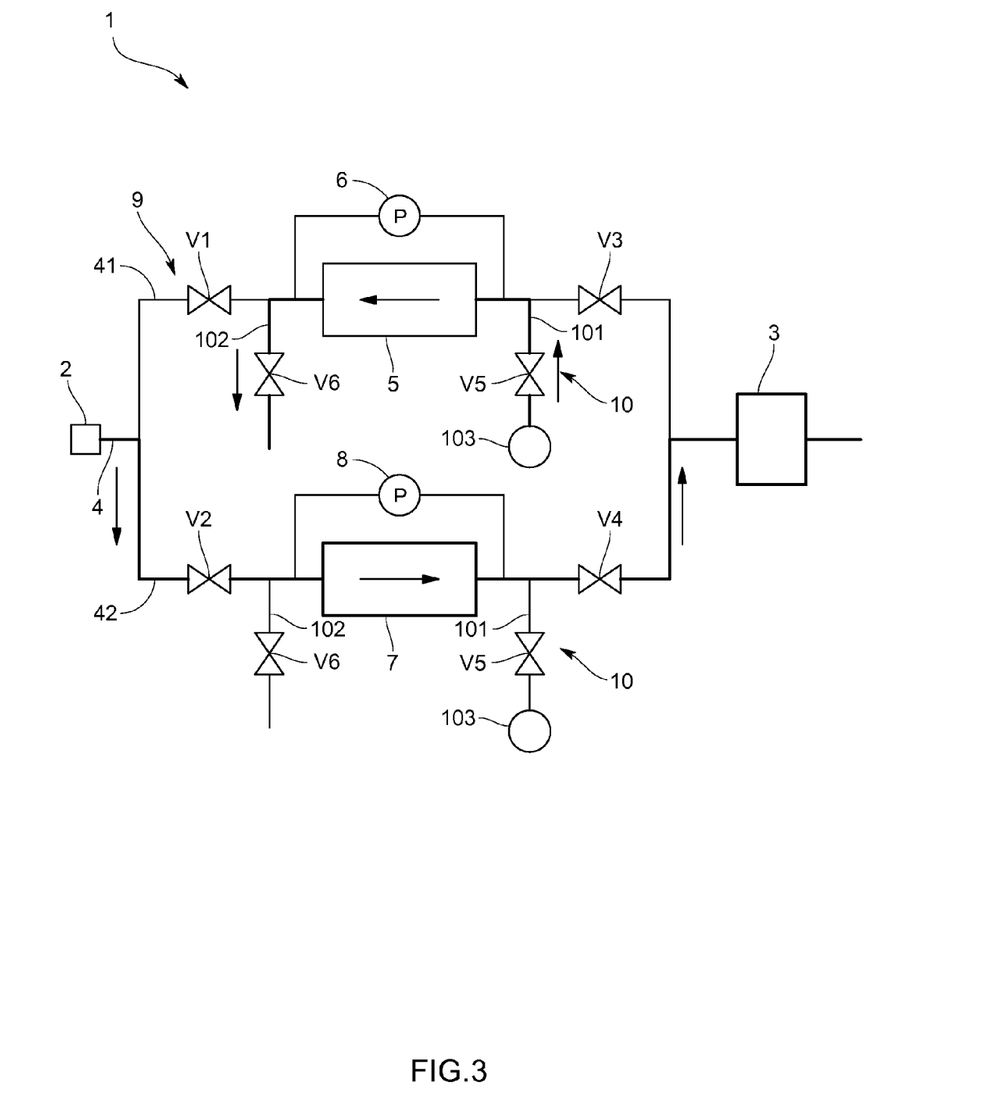
FIG. 3 is a diagram showing a state immediately after switching from the first filter flow path to a second filter flow path.

In the case where the pressure difference indicated by the pressure data falls outside a predetermined range, that is, becomes equal to or larger than a predetermined value, the switching control part 91 of the flow path switching mechanism 9 determines that the first filter 5 is clogged, closes the first upstream side on-off valve V1 and the first downstream side on-off valve V3, and opens the second upstream side on-off valve V2 and the second downstream side on-off valve V4. As a result, as shown in FIG. 3, the filter flow path through which the exhaust gas flows is switched from the first filter flow path 41 to the second filter flow path 42. It is preferred that the first filter 5 and the second filter 7 each includes a filter heating part (not shown), and before the switching, the second filter 7 as a destination is heated to a desired temperature (for example, 191° C.) in advance.

Figure 4:
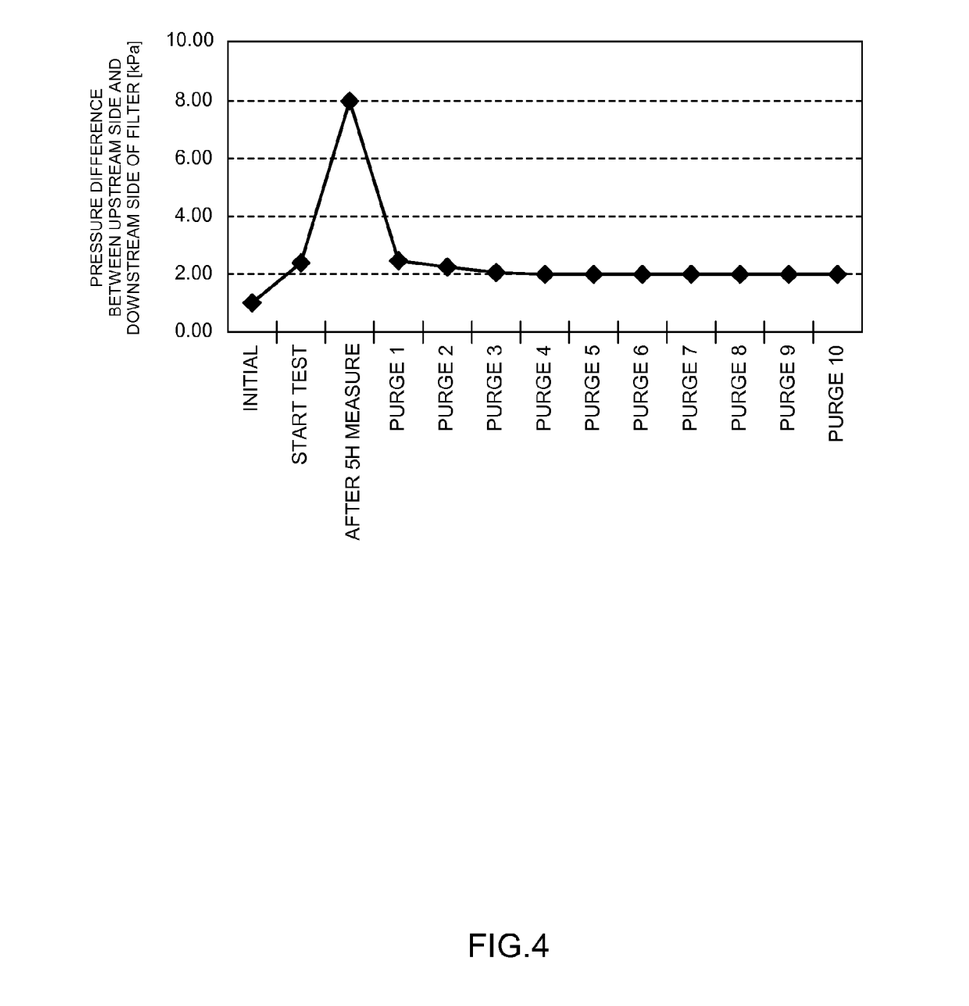
FIG. 4 is a diagram showing variation in the pressure difference between an upstream side and a downstream side of a filter, which is caused by pulsed purge.

Following this switching, the valve control part 105 of pulse purge mechanism 10 acquires a switching signal representing the switching from the switching control part 91, and opens the on-off valve V5 in the purge gas introduction path 101 and the on-off valve V6 in the purge gas lead-out path 102, and the gas supply control part 104 controls the purge gas supplying part 103 to supply the purge gas to the first filter 5 in the pulsed manner. In this manner, the first filter 5 can be washed and recycled. FIG. 4 shows relationship between the number of times of pulsed supply and the pressure difference between the filter upstream side and downstream side. In FIG. 4, the filter can be recovered to the state at a start of measurement by supplying the purge gas in the pulsed manner four times. In the present embodiment, since the first filter 5 and the second filter 7 are heated by the respective filter heating parts (not shown) at all times, even when the pulse purge mechanism 10 supplies the purge gas in the pulsed manner, the first filter 5 is heated. This simplifies removal of a filtered material adhered to the first filter 5. Further, since the first filter 5 and the second filter 7 are heated at all times, even in the case where the flow path switching mechanism 9 irregularly switches between the first filter 5 and the second filter 7, switching to the heated filter is possible.

By repeating the above-mentioned operation, in the continuous measurement of the exhaust gas, "flowing of the exhaust gas in the first filter flow path 41", "detection of contamination of the first filter 5", "switching of the flow path", "flowing of the exhaust gas in the second filter flow path 42 and pulsed purge of the first filter 5", "detection of contamination of the second filter 7", "switching of the flow path", "flowing of the exhaust gas in the first filter flow path 41 and pulsed purge of the second filter 7" are sequentially performed.

In the exhaust gas analyzing apparatus 1 thus configured in the present embodiment, in the case where the pressure difference between the upstream side and the downstream side of the filter (first filter 5) provided in one filter flow path (for example, the first filter flow path 41) through which the exhaust gas flows becomes equal to or larger than the predetermined value due to clogging or the like, the filter flow path through which the exhaust gas flows is switched to the other filter flow path (second filter flow path 42), enabling continuous measurement of the exhaust gas. After switching to the other filter (second filter 7), the purge gas is supplied in the pulsed manner to the one filter (first filter 5) that has clogging or the like and requires washing. Thus, the one filter (first filter 5) can be washed and recycled without being replaced. By sequentially switching between the first filter 5 and the second filter 7 in this manner, continuous measurement can be achieved without suspension due to filter replacement. Further, since the pulse purge mechanism 10 supplies the purge gas in the pulsed manner, the high-pressure gas can be efficiently supplied to the filters 5, 7 without increasing a capacity of the compressor 103 of the pulse purge mechanism 10.

The present invention is not limited to the embodiment. For example, in the embodiment, in the case where the pressure difference acquired by the pressure sensor becomes equal to or larger than the predetermined value, the flow path switching mechanism automatically switches the filter flow path through which the exhaust gas flows. However, it may be configured that the user can select the automatic mode in which the flow path is automatically switched or a manual mode in which the user manually switches the flow path. In this case, the control equipment may include a mode selection signal accepting part for accepting a mode selection signal from the user, and the user may manipulate input means of the control equipment to select the mode. Since the automatic mode or the manual mode can be selected, by selecting the manual mode when focusing on variation in the component concentration or the like, it is possible to prevent the flow path from being automatically switched to temporarily lower the component concentration. Even when the manual mode is selected, in the case where the pressure difference acquired by the pressure sensor becomes equal to or larger than a predetermined value, for example, an alarm may be displayed on a display to inform it to the user. Even in the manual mode, this can prompt the user to switch the filter.

In the embodiment, the pulsed purge of the filter by the pulse purge mechanism is controlled based on the number of times of pulsed supply. However, it may be controlled based on time taken for the pulsed supply. Alternatively, when the pressure difference between the upstream side and the downstream side of the filter becomes equal to or smaller than a predetermined value, pulsed purge of the filter may be finished.

In the embodiment, in performing pulsed purge of the filter, the filter is heated by use of the filter heating part. However, the purge gas itself may be heated to high temperatures (for example, 191° C.), and the high-temperature purge gas may be supplied to the filter in the pulsed manner. This can heat the filter under pulsed purge to promote removal of the filtrated material. Moreover, the purge gas can heat the filter as the destination.

In the embodiment, the first filter and the second filter are heated at all times. However, the filters need not be heated at all times. For example, the filter through which the exhaust gas passes may be heated, the filter as the destination may be previously heated prior to switching, or the purge gas supplied in the pulsed manner may heat the filter.

In addition, the sensor for detecting clogging of the filter may be the pressure sensor for detecting the pressure difference between the upstream side and the downstream side of the filter, a pressure sensor for detecting the pressure on either the upstream side or the downstream side of the filter, or a flow rate sensor for detecting the flow rate in the filter.

Although the engine exhaust gas is analyzed in the embodiment, the exhaust gas discharged from the external combustion engine of a steam turbine and the like may be analyzed.

The present invention is not limited to the embodiment, and as a matter of course, may be variously modified without deviating from its subject matter.

DESCRIPTION OF REFERENCE NUMERALS

1: Exhaust gas analyzing apparatus
2: Introduction port
3: Exhaust gas analyzing part
4: Introduction path
41: First filter flow path
42: Second filter flow path
5: First filter
6: First pressure sensor (first sensor)
7: Second filter
8: Second pressure sensor (second sensor)
9: Flow path switching mechanism
10: Pulse purge mechanism

What is claimed is:

1. An exhaust gas analyzing apparatus for analyzing exhaust gas, the apparatus comprising:
   a first filter flow path provided with a first filter for passing the exhaust gas therethrough and a first sensor for detecting clogging of the first filter;
   a second filter flow path provided with a second filter for passing the exhaust gas therethrough and a second sensor for detecting clogging of the second filter;
   an exhaust gas analyzing part for analyzing combustion byproduct components contained in the exhaust gas passing through the first or second filters;
   a flow path switching mechanism for selectively passing the exhaust gas to the first or second filter flow paths;
   a pulse purge mechanism provided in each of the first and second filter flow paths, the pulse purge mechanism for supplying purge gas to each of the first and second filters in a pulsed manner;
   a first filter heating mechanism for heating the first filter;
   a second filter heating mechanism for heating the second filter; and
   one or more computers programmed to execute
      a switching control part, in the case where an output value of one of the first and second sensors corresponding to one of the first and second filter flow paths through which the flow path switching mechanism is passing the exhaust gas falls outside a predetermined range, for causing the flow path switching mechanism to stop passing the exhaust gas through the one of the first and second filter flow paths and to start passing the exhaust gas through the other of the first and second filter flow paths,
      a pulse purge control part, in the case where the flow path switching mechanism stops passing the exhaust gas through the one of the first and second filter flow paths and starts passing the exhaust gas through the other of the first and second filter flow paths, for causing the pulse purge mechanism to supply the purge gas to one of the first and second filters corresponding to the one of the first and second filter flow paths in a pulsed manner, and
      a filter heater control part for causing a corresponding one of the first and second filter heater mechanisms to heat the other of the first and second filters at least just before the switching mechanism stops passing the exhaust gas through the one of the first and second filter flow paths and starts passing the exhaust gas through the other of the first and second filter flow paths.

2. The exhaust gas analyzing apparatus according to claim 1, wherein a temperature of the purge gas supplied to the one of the first and second filters heats the one of the first and second filters.

3. The exhaust gas analyzing apparatus according to claim 1, further comprising a mode selection signal accepting part for accepting a mode selection signal for switching between an automatic mode and a manual mode, wherein the automatic mode is configured such that the switching control part automatically determines a switching timing for the flow path switching mechanism to switch between the first and second filter flow paths in the case where the output value of the one of the first and second sensors falls outside the predetermined range and wherein the manual mode is configured such that a user can manually determine the switching timing.

4. An operational method of an exhaust gas analyzing apparatus for analyzing exhaust gas, the apparatus including a first filter flow path provided with a first filter for passing the exhaust gas therethrough and a first sensor for detecting clogging of the first filter, a second filter flow path provided with a second filter for passing the exhaust gas therethrough and a second sensor for detecting clogging of the second filter, an exhaust gas analyzing part for analyzing combustion byproduct components contained in the exhaust gas passing through the first or second filters, a flow path switching mechanism for selectively passing the exhaust gas to the first or second filter flow paths, a pulse purge mechanism provided in each of the first and second filter flow paths, the pulse purge mechanism for supplying purge gas to each of the first and second filters in a pulsed manner, a first filter heating mechanism for heating the first filter, and a second filter heating mechanism for heating the second filter, the operational method comprising:

in the case where an output value of one of the first and second sensors corresponding to one of the first and second filter flow paths through which the flow path switching mechanism is passing the exhaust gas falls outside a predetermined range, causing the flow path switching mechanism to stop passing the exhaust gas through the one of the first and second filter flow paths and to start passing the exhaust gas through the other of the first and second filter flow paths,     in the case where the flow path switching mechanism stops passing the exhaust gas through the one of the first and second filter flow paths and starts passing the exhaust gas through the other of the first and second filter flow paths, causing the pulse purge mechanism to supply the purge gas to one of the first and second filters corresponding to the one of the first and second filter flow paths in a pulsed manner, and     causing a corresponding one of the first and second filter heater mechanisms to heat the other of the first and second filters at least just before the switching mechanism stops passing the exhaust gas through the one of the first and second filter flow paths and starts passing the exhaust gas through the other of the first and second filter flow paths.

\* \* \* \* \*